United States Patent
Bergh et al.

[11] Patent Number: 5,817,006
[45] Date of Patent: Oct. 6, 1998

[54] METHOD AND APPARATUS FOR MEASUREMENT OF EATING SPEED

[75] Inventors: Cecilia H. Bergh; Per H. Söderstein, both of Stockholm; Ståle F. Ekelund, Bromma, all of Sweden

[73] Assignees: Cecilia Bergh; Per Sodersten, both of Stockholm, Sweden

[21] Appl. No.: 776,402

[22] PCT Filed: Jun. 29, 1995

[86] PCT No.: PCT/SE95/00806

§ 371 Date: May 13, 1997

§ 102(e) Date: May 13, 1997

[87] PCT Pub. No.: WO96/02183

PCT Pub. Date: Feb. 1, 1996

[30] Foreign Application Priority Data

Jul. 16, 1994 [SE] Sweden .................................. 9402488

[51] Int. Cl.[6] .................................................. G06F 15/00
[52] U.S. Cl. ............................................................. 600/300
[58] Field of Search .................... 600/300; 128/920–924; 434/127

[56] References Cited

U.S. PATENT DOCUMENTS

| | | | |
|---|---|---|---|
| 4,924,389 | 5/1990 | Gerbaulet et al. | 600/300 |
| 5,233,520 | 8/1993 | Kretsch et al. | 128/921 X |
| 5,388,043 | 2/1995 | Hettinger | 128/921 X |

OTHER PUBLICATIONS

Kissileff et al., Universal eating monitor for continuous recording of solid . . . in man, The American Physiological Society, 1980, pp. R14–R22.

Kissileff et al., A quadratic Equation Adequately Describes . . . in Man, Appetite: Journal for Intake Research, 1982, 3, 255–272.

Hetherington et al., Methods of Investigating Human Eating Behavior, Feeding and Drinking, 1987 Elsevier Science Publishers B.V. (Biomedical Division), Chapter 4, pp. 77–109.

Borg, Scale With Radio Properties For Intermodel and . . . , Psychophysical Judgment and the Process of Perception, Berlin; VEB Deutscher Verlag der Wissenchaffen, 1982.

Holland et al., Measurement of Excessive Appetite and Metabolic Changes in Prader . . . International Journal of Obesity (1993) 17, 527–532.

Primary Examiner—John P. Lacyk
Assistant Examiner—Samuel Gilbert
Attorney, Agent, or Firm—IP Group of Pillsbury Madison & Sutro LLP

[57] ABSTRACT

A method and a device for the measurement of rate of eating of an object of measurement ingesting food. The method includes a scale for the measurement of food intake and a computer system, which is signal-connected with the scale and allows storing and computing of signals and visualization of stored and computed signals. Simultaneously, the computer system provides at least one reference standard for the rate of eating and an associated, biologically determined level of satiety, which is used for comparison, visualization and evaluation together with the values of rate of eating recorded by said scale and stored by the computer system. This allows for adjustment of rate of eating. The computer system of the method may be provided as a portable computer with an integrated scale.

16 Claims, 3 Drawing Sheets

METHOD AND APPARATUS FOR MEASUREMENT OF EATING SPEED

This application is the national phase of international application PCT/SE95/00806, filed Jun. 29, 1995 which designated the U.S.

FIELD OF THE INVENTION

The present invention pertains to a measuring device for the simultaneous measurement of the rate of eating behavior and the associated perception of satiety in a measuring object during the ingestion of food.

DESCRIPTION OF RELATED ART

There is a long-standing need to control food intake and body weight, because overweight and obesity, for instance, are serious health problems. Given this starting point it is of considerable importance to develop methods for the measuring of eating behavior and the experience of satiety.

Rate of ingestive behaviour

Ingestive behavior has been studied by Kissileff et al. (Kissileff H R, Klingsberg G, Van Itallie T B (1980), "Universal eating monitor for continuous recording of solid or liquid consumption in man", American Journal of Physiology 283: R14–R22), who used a plate placed on a scale, that was lowered in the surface of a table and connected to a computer. During a meal, the computer recorded the weight reduction of the plate from which the food was eaten. Using this method, the rate of ingestion could be estimated. It was concluded that eating rate is stable within individuals and variable between individuals. Kissileff et al. (Kissileff H R, Thornton J, Becker E (1982), "A quadratic equation adequately describes the cumulative food intake curve in man", Appetite 3:255–272), suggested that eating rate in man, measured with the above procedure, can be described using a quadratic function. No alternatives have been suggested. There is, however, no biological support or foundation for the hypothesized quadratic function. That is to say, there is no biological factor that controls the rate of ingestion such that, during a meal, the rate of ingestion can be described by a quadratic function, because of the variation in the biological factor. Measuring the rate of ingestion is of considerable importance, in as much as alteration in this rate may be causally related to the development of obesity (Hetherington M, Rolls B (1987) "Methods of investigating human eating behavior. In: Toates F M, Rowlands N E (eds.): "Eating and Drinking", pp 77–109, Elsevier; Amsterdam).

Satiety

There is, however, an equally large interest in measuring and controlling satiety. A change in the perception of satiety can also be the reason for developing obesity. Conventionally, the person participating in an experiment is asked to estimate her/his satiety before and after a meal utilizing a visual analog scale, that is to say the person uses paper and pen to note how intense, on a continuum from low to high, she/he experiences her/his level of satiety.

Psychophysical studies of the subjective estimation of work load have been performed by Borg (Borg G (1982), "A category scale with ratio properties for intermodal and interindividual comparisons", In: Greissler H-G, Petzold Y M (eds): "Psychophysical Judgement and the Process of Perception", pp 25–34, Springer Verlag: Berlin). Borg constructed a scale, that generates data on the level of an interval scale, that is to say a scale with equal steps. At the same time as the person participating in an experiment eats from her/his plate, placed on the scale as described above, this judgement scale is displayed on a monitor. According to this scale the level of satiety can vary from very weak, which is equivalent to 0–0.5, to very strong, which is equivalent to 10.

SUMMARY OF THE DISCLOSED INVENTION

The present invention is based on an alternative and a further development of the measurement of eating rate, in that different rates of ingestion correspond to a biologically determined degree of satiety. Eating rate is measured utilizing the variables (weight of food, time) and for the quantification of satiety the interval scale of Borg is used. The invention makes use of reference standards (standard curves or curves of normality), obtained from research on healthy individuals. These curves reflect the average rate of ingestion that has been found statistically significant through the investigation of groups, differing in, for example, age and weight, within the population of men and women. The interval scale of Borg is used to record satiety.

The object of the invention is to develop a measuring device that allows, among others, the obese to gain access to a method for weight control. Overweight and obesity is a major health problem, and the overweight, therefore, have an obvious interest in such a device. Furthermore, the control of body weight and ingestive behavior is of considerable importance to athletes and those engaged in sports. A method for the control of body weight and eating behavior is also needed within clinical medicine to care for patients suffering from anorexia, bulimia and gastrointestinal discomfort, that is to say disorders related to the intake of food. Use of the present method and device is, however, probably not limited to these groups, but is likely to be of importance to those within the general public who are at risk to develop disorders of body weight control.

A device to assist in the control of body weight provides the individual with a possibility to control eating behavior and the perception of satiety and, therefore, a method to control body weight. According to the invention, this is accomplished by the display of the reference standards mentioned above, on a monitor or via a printing unit. The reference standards for eating behavior and satiety as a function of eating rate are derived from biologically based mean values obtained through research on samples of individuals from the general population. Using this device, the individual is in a position to adapt her/his eating behavior and perception of satiety to what, by definition, is normal through the selection of the proper reference values and by adapting her/his rate of ingestion to the reference value displayed on a medium, for example a monitor, in real time. The rate of ingestion of the individual is displayed simultaneously with the reference standard and the two are thereby displayed so as to overlap.

Persons participating in the development of the invention and displaying deviations from the reference standards with respect to eating behavior and perception of satiety have considered themselves unable or ignorant as to how to eat and how to feel satiated. Therefore, a device in a system according to the invention should be of considerable importance to a user with a need to control her/his food intake.

The method on which the present invention is based makes possible, what has previously been unknown, simultaneous registration and display of rate of eating and, at the same time, adjustment of satiety to a standard of reference, shown at the same time as the eating rate of the person. An observer and/or a user is thus in a position to modify, correct, verify, investigate etc her/his ingestive behavior in real time. Repeated measurements on a considerable number of men and women have shown that the method of the present invention generates stable values and reacts to a biological challenge, deprivation of food, that is to say the time without food that has elapsed before the time of measurement.

To meet the object of the invention, the invention also includes a method to measure the rate of ingestion of a person eating a meal. The method utilizes a scale to measure the intake of food and a first means signal connected with the scale, for communication, computing and visualization of signals and for storing previously computed signals. The first means provides at least one reference standard for rate of ingestion and, in connection with each standard, a related specific, biologically based, level of satiety. This standard is used for comparison, visualization and evaluation of the measures of food intake, which have been obtained and stored in the first means, and to make it possible to adjust to a change in the rate of eating. To this aim the following steps should be taken:

choice of reference standard, via the first means, for rate of eating. The standard and its satiety scale is visualized to allow one or several observers, including the person ingesting the food, to monitor an ongoing measurement;

placement of a second means, for storing the food, on the scale and the placement of food on this device;

allowing the scale to stabilize;

initiation of a period of measurement of rate of eating when the person eats the food from the second means, a moment at which each measure of the intake of food is stored, computed and visualised;

food is replenished as needed to allow for continued measurement; and a modification of the rate of eating, based on the standard of reference in relation to the actual rate of eating during the meal, can be introduced during the period of measurement.

Moreover, the method includes the establishment of reference standards concerning the rate of eating and, correlatively, the development of satiety and the pattern of secretion of gastrointestinal hormones. Furthermore, the reference standards are based on the effects of deprivation of food on the rate of eating, the development of satiety and the pattern of secretion of gastrointestinal hormones, such that the perception of satiety will wane in correlation with declining levels of these hormones. Eating behavior and the perception of satiety is tested anew as soon as the experience of satiety has resumed its initial value. The octapeptide of cholecystokinin (CCK-8), in particular, is a determinant of satiety, such that its pattern of secretion and the level of deprivation of food affects the rate of eating to become negatively accelerated and the experience of satiety positively accelerated with an increase in deprivation. According to the above summarized method, reference standards can be developed, based on repeated testing of groups of individuals, large enough to permit establishment of statistical significance.

Visualization of the reference standard of eating behavior and the measured eating rate will mainly be through the same medium (a monitor, a printer, or some such), so as to facilitate visual comparison by the observer. When needed, the first means can deliver an evaluation of satiety during the period of measurement of choice, e.g. via the monitor. The second means is preferably a household device for serving food, that is to say a plate, a bowl or a serving plate.

To serve its purpose, the invention includes a method to register the rate of eating displayed by a measuring object during the periods of eating to be measured. The method includes a scale for the measurement of food intake, and a first means, signal connected with the scale, for storing and computing signals and visualization of these stored and computed signals. A second means, for storage of food, is placed on the scale. The measuring object eats the food, whereby the scale detects the signals generated by the first means, which then delivers at least one standard of reference for eating rate and one standard of a biologically determined level of satiety, and its associated numerical value. The reference standards can be utilized for comparison, evaluation and visualization together with the measures delivered by the scale and stored in the first means, thus allowing measures to compensate and change the rate of eating.

As mentioned above, a display of the reference standard and the recorded rate of eating can be made through the same medium to facilitate visual comparison for the observer and to make possible that the first means deliver an evaluation of the level of satiety and eating rate during any period of measurement. For example, through, by preference, a Cartesian system of coordinates displayed on a monitor the satiety scale will be related to the reference standard of eating rate along with the recorded rate of eating (FIG. 3, below).

In the present embodiment, the scale is a peripheral device in relation to the computer.

In a further embodiment, the first means is a computer and the scale is integrated with a central unit in the computer.

According to another embodiment, the central unit consists of a portable computer with the scale integrated, that is to say the keys have been replaced by the scale. The scale is internally and serially connected to the computer.

Placement of a second means on the scale, implies that the second means should be possible to disconnect or should be connected to the scale, as described further below.

BRIEF DESCRIPTION OF THE DRAWINGS

The invention will be described in the following by reference to non limiting embodiments illustrated in the associated figures. For equivalent references between figures the same reference numerals will be used.

In the drawings

DETAILED DESCRIPTION OF PREFERRED EMBODIMENTS

According to the scientific papers mentioned above and to ongoing research in our laboratory, aiming at mathematical models of eating behavior and the perception of satiety, there is no a priori reason for the selection of any mathematical model in particular, for example a quadratic model. This appears particularly true considering the great interindividual biological variability. Furthermore, a quadratic equation has not been found of optimal fit.

Because the factors that control the rate of eating and the perception of satiety are largely unknown, models of eating behavior and satiety should rely on biologically based hypotheses. Two biological factors of interest are the level of deprivation of food and the pattern of secretion of gastrointestinal hormones, in particular that of the octapeptide of cholecystokinin (CCK-8). The degree of deprivation should be varied and the eating behavior and the perception of satiety should be related to the secretion of CCK-8 so that the decline in the level of satiation is measured and correlated to the concentration of CCK-8 in the blood. The eating behavior and the perception of satiety is tested once more as soon as the level of satiety has returned to its basal value.

According to one hypothesis, which is the basis of the present invention, eating behavior is determined by the level of deprivation and by CCK-8, such that the rate of eating is negatively accelerated after a long period of deprivation and that the perception of satiety is positively accelerated as shown by a graphical display of a curve. Studies on animals have demonstrated such a relationship between the duration of satiety and blood levels of CCK-8.

To allow establishment of standards of reference for eating behavior, rate of eating and perception of satiety data will be collected from large groups of girls, boys, women and men. This will make possible quantitative description of behavior and perception in all age groups of the population under the conditions discussed above.

Figure 1:
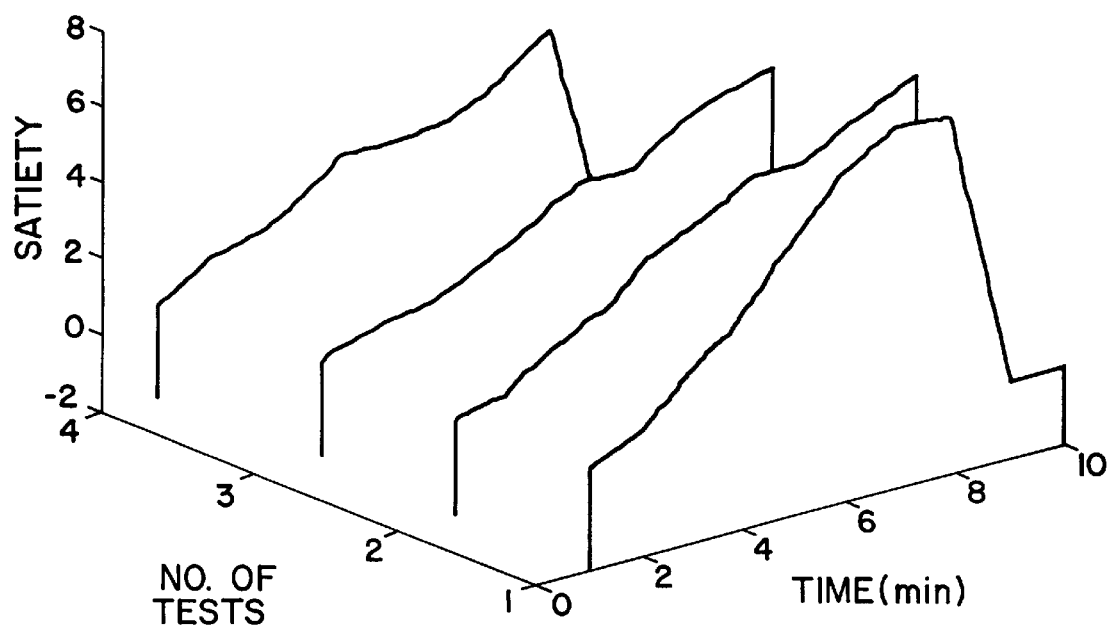
FIG. 1 shows a graphical example of an estimated level of satiety of a person tested under varying conditions using the scale of satiety according to the invention.

An example of repeated estimation of satiety using the presently discussed rating scale is shown in FIG. 1, which is based on measures taken from an individual tested three times under the same conditions and a fourth time when the individual had abstained from dinner on the preceding day. The curves confirm the findings of Kissileff et al. (1980), that showed that eating behavior is relatively consistent within individuals.

Figure 2:
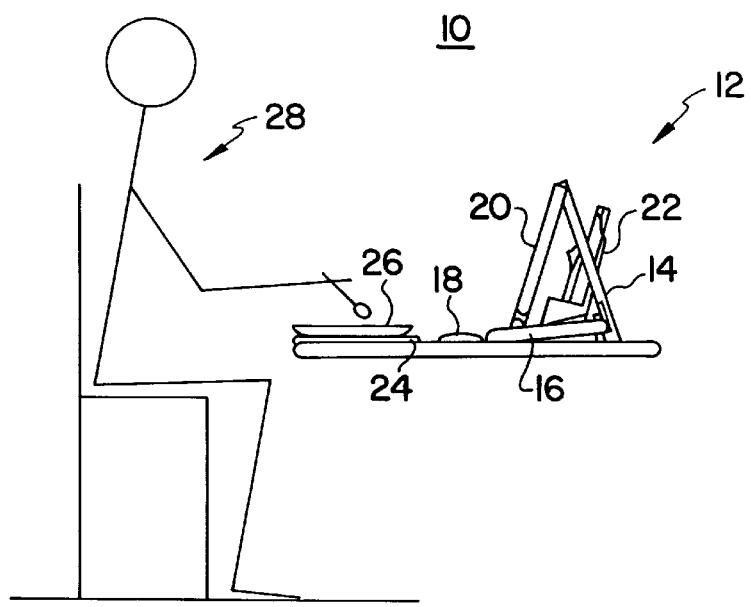
FIG. 2 shows a method including a computer system in which a scale is a peripheral part of the computer system.

FIG. 2 shows a measuring device 10 with a first means 12, in this case a computing system, with a computer 14 and a peripheral equipment, including a key panel 16, a mouse 18, a steering ball or a pointing device (not shown), a monitor 20 and a printer 22. The scale 24, that is included in the measuring device, is also peripheral to the computing system 12, according to the invention signal connected to the computing system 12, for example via the serial communication port. The term signal connected implies that the connection, apart from being mediated via a cable, may be wire less by means of known technology (not shown), for example infrared, radio or the like technology. The scale 24, preferably a digital one although others are conceivable, need not be connected to the computer by any special adaptation. An analogous scale demands an adaptation device for sampling, quantification and analog/digital conversion.

The protocols and the units of the present invention do not demand new technology of computing or communication. The required technology of the present invention is known to those skilled in the art of computer technology and need not be elaborated here. Any computing system, that is available on the market, e.g. PC; Macintosh, portable computers or other, can be adapted. However, the method to utilize the invention and the measuring device, the computer system included, is a unique innovation.

Utilization of the measuring device 10 requires a second means 26 for the presentation of food, from which the user and measuring object 28, for example an athlete preparing for a big athletic competition, ingests food. It is possible for the athletic supervisor to participate as an observer. This means 26 is, most suitably, a common piece of household, such as a plate, a bowl or a serving plate.

To carry through a test with the measuring device 10 the program that controls the measurement is started, for example via the mouse 18, the steering ball or the key panel 16. It is also possible to start measuring when the means 26 is placed on the scale 26. Thereafter, the above-described method is started to complete a test. If placement of the means 26 does not initiate the measurement, the user 28 places the means 26, i.e. the plate 26, on the scale, and, thereafter, starts the measurement and the selection of reference standards 30, solid line of eating behavior in FIG. 3 via the mouse. The interval scale of satiety included in FIG. 3, which shows 8 of the 10 intervals. The satiety is recorded at specified time points of the curve of eating rate. The lengths of the intervals is dependent of the biologically based perception of satiety in relation to the proper reference standard. As mentioned satiety is determined by the rate of eating and mediated by the biological factors mentioned above.

Figure 3:
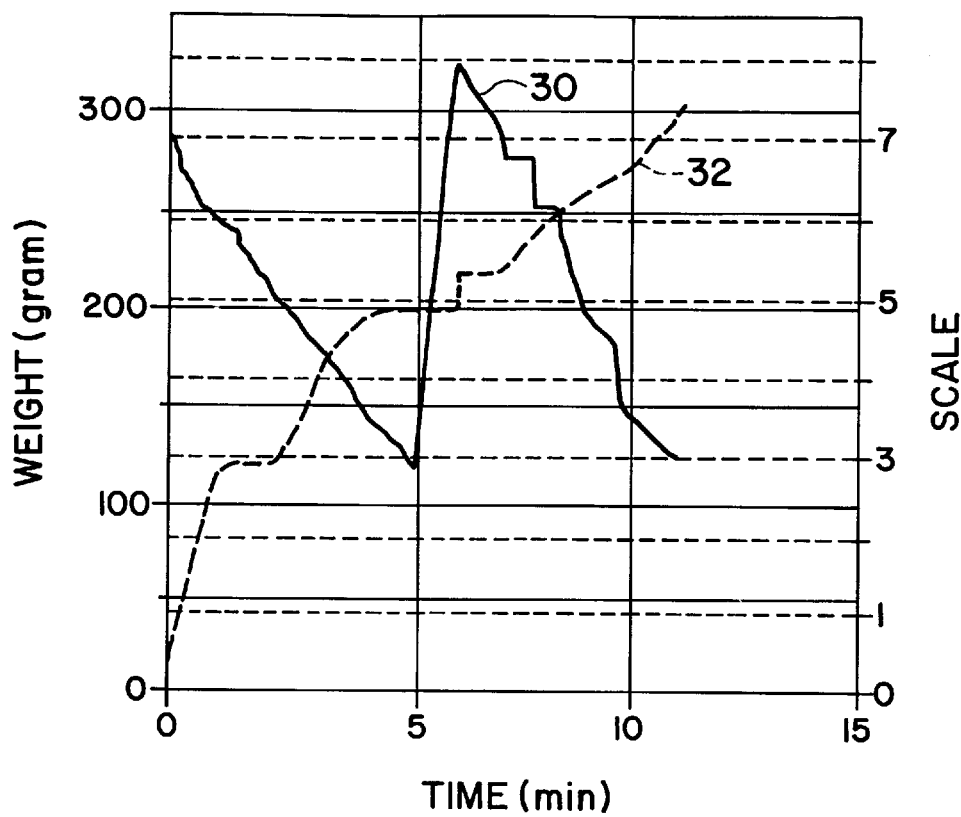
FIG. 3 shows a display on a monitor with a standard curve of reference including a scale of satiety and an overlapping curve with actual measures of eating rate from an object of measurement from a test according to the invention.

A period of measurement can also be initiated via the key panel 16, but normally this is done only when retrieving data and when updating programs. The standard of reference becomes visible on a picture medium that is connected to the device, in this case the monitor of the computing system 20. If the user or the observer want the method to run "blind", it might be feasible not to display the standard to the user but store it in the computer for printout, for example via a printer or delayed printout, and the associated evaluation of the obtained rates of ingestion in relation to the standard of reference or other evaluations, such as evaluation of rating of satiety and statistical analyses. "Blind" measurement can also be accomplished by turning the monitor 20 away from the measuring object and permit only the observer to follow the method. After the start of a period of measurement and placement of the plate 26 on the scale the food (not shown), which is selected according to the reference standard, is placed on the plate, stabilization of the scale is allowed for some seconds and the user 28 starts eating. The rate of ingestion 32, the dotted line in FIG. 3, is then displayed over or overlapping the standard of reference on the monitor 20 thus making comparison in real time immediately possible, and allowing measures, such as modifying the rate of ingestion, for adapting to the reference standard to be taken. Addition of food is made with reference to the standard 30, for example by clicking the mouse at regular time intervals which results in a display of information on how much food should be provided. The method is terminated preferably by lifting the plate 26 from the scale 24. The results of the measurement are stored internally in one or several files, for later use, in the central unit 14 or in an external storage medium via one of the communication ports of the central unit (not shown).

The scale 24 will be subjected to unwanted pushes and unbalance when in use.

Therefore, the following measures will be taken:

i) The proper starting weight will be ensured (including a reasonable tolerance, e.g. 1 g).

ii) A weight below the previous will be rejected.

iii) A weight above that of a mouthful will be rejected.

In the present example, the weight of a mouthful is estimated to 25 g. When a meal is started, the user serves food until the proper amount of food, determined by the reference standard, has been served. Before starting to eat, however, the scale must be stable to ensure the correct starting weight. In the pseudo code for filtering of erroneous values, shown below, the reference weight, i.e. the preceding weight is referred to as ($v_0$) the recorded weight as ($v_n$) and the weight of a mouthful as (g).

```
Pseudo code:
IF (v_n ≧ v_0-g) AND (v_n ≧ v_0) THEN
   BEGIN
      WRITE(resfile, v_n) 'store recorded weight in result file'
      v_0 = v_n
   END
```

Figure 4:
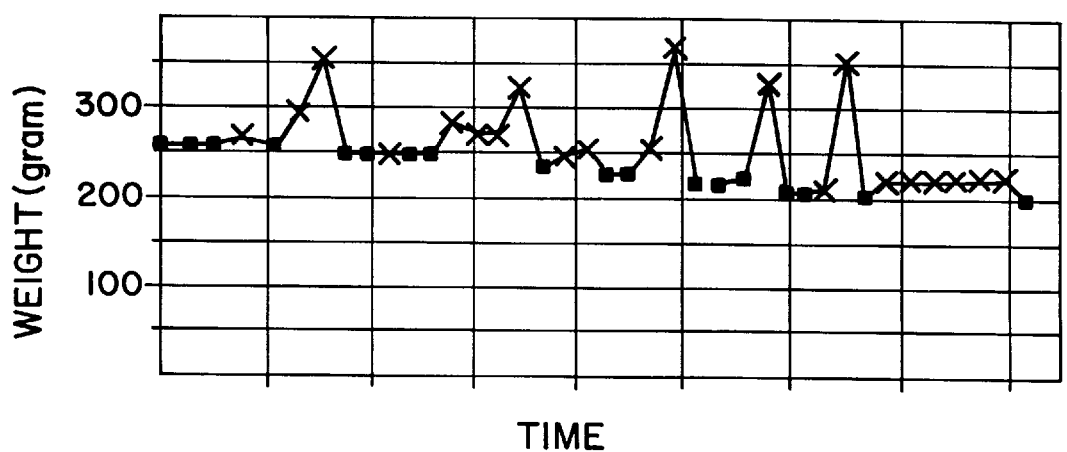
FIG. 4 shows filtering of errors according to the invention.

In FIG. 4, cross marked points are erroneous measured and filtered away according to the algorithm in the pseudo code.

Figure 5:
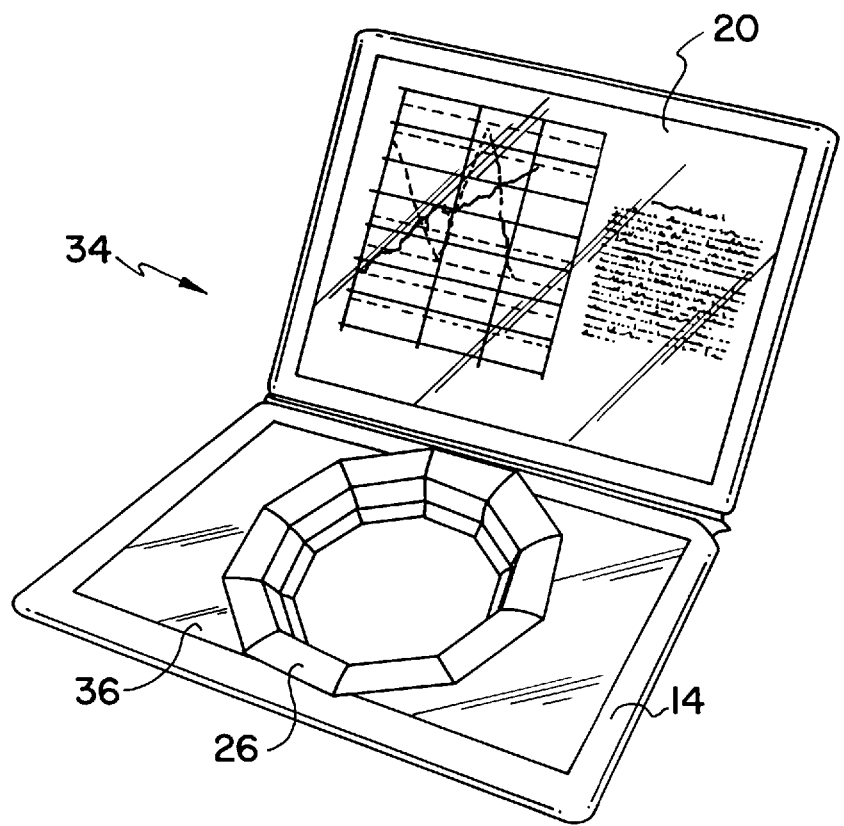
FIG. 5 shows a scale that has been integrated with a portable computer according to the invention.

In another version of the computer system 12 according to the present invention, with reference to FIG. 5, the central unit 14 consists of a portable computer 34 with a monitor 20. To serve its purpose, the portable computer 34 has been made "user-friendly" by means of a new and innovative re-construction, i.e. the key panel has been replaced by a digital scale, including a plate 36. The scale is internally and serially connected to the portable computer. Apart from that, the modified measuring device with the portable computer 34 as the central unit 14 works identically with the measuring device 10 described above and according to the present invention. It is easily recognized that a key panel can be connected to the computer 34 via some of its communication ports, as needed. Most commonly, however, the method including choice of reference standard 30, addition of food etc, is started via a mouse, track ball or pointing device.

It is also possible to have the second means 26 for serving food permanently connected or removable on the plate 36 of the scale 24. This applies to both versions of the design of the measuring device 10. This can be made possible by the use of a vacuum suction device, a magnetic device or an equivalent device for removable mounting. In the case of a permanent mounting of the second means 26 for serving food, removal of the plate of the scale 36 makes this possible.

The embodiments of the present invention described above are not intended to limit variations within the claims of the invention. Other possibilities are likely to be apparent to those skilled in the art of the relevant technologies.

What is claimed is:

1. A method for measuring the rate of ingestive behavior of a measuring object ingesting food, comprising:

using a scale to measure food intake by the object;

using a computer system connected to the scale for storing and computing signals, and for visualizing stored and computed signals;

said computer system providing at least one reference standard for rate of ingestion, and an associated reference standard of a specific, biologically determined level of satiety, derived from a scale of satiety;

using said rate of ingestion for comparison, visualization and evaluation, together with results from use of said scale to measure food intake by the object, as stored in said computer system; and adjusting eating behavior of the object, in real time, by:
choosing a reference standard from among those provided by said computer system, for a rate of ingestion having an associated scale of satiety, and using the computer system for visualizing the chosen reference standard, for thereby enabling at least one observer to follow an ongoing sequence of measurements;

placing a food storage article on said scale, and placing an amount of food on said food storage article;

awaiting stabilization of said scale following said placing of said food storage article and quantity of food;

initializing a period of measuring of rate of eating, in which said object takes and east a plurality of successive bits of food from said quantity, from said storage article, and, during said period performing said storing, computing and visualizing by said computer system in relation to each said bit of food;

if, as a result of said eating said food storage article becomes depleted of food during said period, replenishing said food storage article at least once with a further amount of food, for enabling continuation of said period; and introducing, at a time during said period, a change in the rate of eating by the object as therefore practiced by the object during said period, to a new rate of eating, said new rate of eating being based on a selected one of said at least one referenced standard.

2. The method of claim 1, further comprising:

establishing said at least one reference standard for rate of ingestion, and an associated reference standard of a specific, biologically determined level of satiety, by basing these standards on lengths of period of food deprivation in a text object and patterns of secretion of at least one gastrointestinal hormone by the test object.

3. The method of claim 2, wherein:

said establishing comprises depriving the test object of food for various lengths of period, measuring corresponding patterns of secretion of at least on gastrointestinal hormone by the test object, and making corresponding observations as to the perception of satiety in the test object.

4. The method of claim 3, wherein:

said establishing comprises correlating declines in perception of satiety of the text object with concentration of at least one gastrointestinal hormone in the blood of the test object.

5. The method of claim 4, wherein:

said establishing comprises repeatedly depriving the test object of food in a succession of tests, between each of which the perception of satiety of the test object is observed, as part of said making corresponding observations, to have returned to a basal value.

6. The method of claim 2, wherein:

said at least one gastrointestinal hormone is the octapeptide of cholecystokinen (CCK-8).

7. The method of claim 6, wherein:

said change in rate of eating is introduced such as to negatively accelerate rate of eating while positively accelerating perception of satiety.

8. The method of claim 2, further comprising:

performing said visualizing of a selected one of said at least one eating standard, and recorded actual rate of eating by the object simultaneously on a same medium; and visually comparing said selected eating standard and said actual rate of eating as visualized on said same medium.

9. The method of claim 2, further comprising:

said computer system continuously providing an evaluation of at least one of perception of satiety of the object and actual rate of eating by the object during said period.

10. Apparatus for measuring rate of eating by an object who is ingesting food, comprising:

a scale arranged for measuring food intake by the object;

a signal storing, computing and visualizing device which is signal-connected to said scale and arranged for storing signals including signals received from said scale, for computing signals received by said device, including from said scale, and for visualizing signals stored and computed by said device;

a food storage article arranged to be supported on said scale for storing food to be consumed by said object;

said scale being arranged to register intake of food and to provide signals to said device corresponding to such registering of intake;

said device being arranged to provide said object with at least one reference standard for rate of eating, each said standard being correlated with a biologically determined level of satiety on a scale of satiety;

said device being arranged for comparing, evaluating, and visualizing simultaneously on a same medium actual rate of eating as recorded by said device and said at least one standard; and said device being arranged for varying rate of eating by said object during a period of measurement.

11. The apparatus of claim 10, wherein:

said device is arranged to provide an evaluation of at least one of level of satiety of the object and rate of eating by the object during said period.

12. The apparatus of claim 10, wherein:

said device is a computer system.

13. The apparatus of claim 12, wherein:

said scale is integrated with a central unit on said computer system.

14. The apparatus of claim 13, wherein:

said central unit of said computer system is a portable computer.

15. The apparatus of claim 12, wherein:

said scale is provided a peripheral part in relation to said computer system.

16. The apparatus of claim 10, wherein:

said article is a household food serving article.

* * * * *